(12) United States Patent
Prabakaran et al.

(10) Patent No.: US 8,795,986 B2
(45) Date of Patent: Aug. 5, 2014

(54) MICROBIAL METHOD FOR THE BIOTRANSFORMATION OF COLCHICINOID COMPOUNDS

(75) Inventors: Krishnamurthy Prabakaran, Karnataka (IN); Sankarasubramanian Kanagavelrajan, Karnataka (IN); Nallasamy Mohanasundaram Kannamapuram, Karnataka (IN); Ayyappan Hariharan Kooakarakkaran, Karnataka (IN); Bhimaraju Poliseti, Karnataka (IN)

(73) Assignee: Sequent Scientific Ltd., Thane (W), IN (US)

( * ) Notice: Subject to any disclaimer, the term of this patent is extended or adjusted under 35 U.S.C. 154(b) by 0 days.

(21) Appl. No.: 13/825,084

(22) PCT Filed: Sep. 22, 2011

(86) PCT No.: PCT/IN2011/000660
§ 371 (c)(1),
(2), (4) Date: Mar. 19, 2013

(87) PCT Pub. No.: WO2012/038982
PCT Pub. Date: Mar. 29, 2012

(65) Prior Publication Data
US 2014/0024080 A1    Jan. 23, 2014

(30) Foreign Application Priority Data

Sep. 22, 2010 (IN) .......................... 2760/CHE/2010

(51) Int. Cl.
  C12P 19/56    (2006.01)
  C12N 1/20    (2006.01)
(52) U.S. Cl.
  USPC ........................................ 435/78; 435/252.1
(58) Field of Classification Search
  USPC ................................. 435/78, 252.1
  See application file for complete search history.

(56) References Cited

U.S. PATENT DOCUMENTS

| 6,150,140 A | 11/2000 | Bombardelli et al. |
| 6,372,458 B1 * | 4/2002 | Bombardelli et al. .......... 435/74 |
| 2009/0011479 A1 | 1/2009 | Ponzone |

FOREIGN PATENT DOCUMENTS

GB           923421          4/1963

OTHER PUBLICATIONS

Davis, "Microbial Transformations of N-methylcolchiceinamide" Antimicrob. Agents Chemother., Mar. 1981; vol. 19, No. 3, pp. 465-469 (Absract).
International Search Report for PCT/IN2011/000660 (WO2012/038982) dated May 21, 2012.
Solet et al., Glucosylation of thiocolchicine by a cell suspension of culture of *Centella asiatica*. Phytochemistry. vol. 33, Issue 4, Jul. 6, 1993, pp. 817-820.
Hufford et al., Microbial transformations and C-NMR analysis of colchicine. Journal of Pharmaceutical Sciences, vol. 68, Issue 10 pp. 1239-1243, Oct. 1979.

* cited by examiner

*Primary Examiner* — Rosanne Kosson
(74) *Attorney, Agent, or Firm* — Kramer Amado, P.C.

(57) ABSTRACT

The invention relates to a method for the Bio-transformation of Thiocolchicine a colchicinoid compound into its glycosylated form using a selective microorganism *Providencia vermicola*. Use of bacterial strain, *Providencia vermicola* for microbial bio-transformation of thiocolchicine (TCN) to their corresponding 3-0-glycosyl derivative as well as specific strains of that species *Providencia vermicola* for microbial transformation of other colchicinoid compounds such as colchicine, thiocolchicine, 3-demethylcolchicine, 3-demethylthiocolchicine and N-deacetylthiocolchicine to its corresponding glycosylated form and subsequent isolation of the transformed compounds from the bacterial culture medium is disclosed. *Providencia vermicola* (MTCC 5578) a gram negative bacteria has been identified having trans-glycosylation ability and convert thiocolchicine (TCN) to Thiocolchicocide (TCS).

15 Claims, 1 Drawing Sheet

SEQUENCE LISTING

<110> Elysian Life Sciences Private Limited.

<120> A Microbial Method For The Biotransformation Of Colchicinoid Compounds

<140> 2760/CHE/2010

<141> 22/09/2010

<160> Number of SEQ ID NOS: 1

<210> SEQ ID NOS: 1

<211> LENGTH: 1491

<212> TYPE: rRNA

<213> ORGANISM: *Providencia vermicoloa* (MTCC 5578)

<222> (1)... (1491)

<400> Sequence-1

| | | | | | | |
|---|---|---|---|---|---|---|
| tcagattgaa | cgctgcggca | ggcctaacac | atgcaagtcg | agcggtaaca | ggggaagctt | 60 |
| gcttcccgct | gacgagcggc | ggacgggtga | gtaatgtatg | gggatctgcc | cgatagaggg | 120 |
| ggataactac | ggaaacggtg | gctaataccg | cataatctct | taggagcaaa | gcagggggaac | 180 |
| ttcggtcctt | gcgctatcgg | atgaacccat | atgggattag | ctagtaggtg | gggtaatggc | 240 |
| tcacctaggc | gacgatccct | agctggtctg | agaggatgat | cagccacact | gggactgaga | 300 |
| cacggcccag | actcctacgg | gaggcagcag | tggggaatat | tgcacaatgg | gcgcaagcct | 360 |
| gatgcagcca | tgccgcgtgt | atgaagaagg | ccctagggtt | gtaaagtact | ttcagtcggg | 420 |
| aggaaggcgt | tgatgctaat | atcatcaacg | attgacgtta | ccgacagaag | aagcaccggc | 480 |
| taactccgtg | ccagcagccg | cggtaatacg | gagggtgcaa | gcgttaatcg | gaattactgg | 540 |
| gcgtaaagcg | cacgcaggcg | gttgattaag | ttagatgtga | aatccccggg | cttaacctgg | 600 |
| gaatggcatc | taagactggt | cagctagagt | cttgtagagg | ggggtagaat | tccatgtgta | 660 |
| gcggtgaaat | gcgtagagat | gtggaggaat | accggtggcg | aaggcggccc | cctggacaaa | 720 |
| gactgacgct | caggtgcgaa | agcgtgggga | gcaaacagga | ttagataccc | tggtagtcca | 780 |
| cgctgtaaac | gatgtcgatt | tggaggttgt | gcccttgagg | cgtggcttcc | ggagctaacg | 840 |
| cgttaaatcg | accgcctggg | gagtacgcc | gcaaggttaa | aactcaaatg | aattgacggg | 900 |
| ggcccgcaca | agcggtggag | catgtggttt | aattcgatgc | aacgcgaaga | accttaccta | 960 |
| ctcttgacat | ccagagaact | tagcagagat | gctttggtgc | cttcgggaac | tctgagacag | 1020 |
| gtgctgcatg | gctgtcgtca | gctcgtgttg | tgaaatgttg | ggttaagtcc | cgcaacgagc | 1080 |
| gcaacccttta | tcctttgttg | ccagcgattc | ggtcgggaac | tcaaaggaga | ctgccggtga | 1140 |
| taaaccggag | gaaggtgggg | atgacgtcaa | gtcatcatgg | cccttacgag | tagggctaca | 1200 |
| cacgtgctac | aatggcgtat | acaaagagaa | gcgacctcgc | gagagcaagc | ggaactcata | 1260 |
| aagtacgtcg | tagtccggat | tggagtctgc | aactcgactc | catgaagtcg | gaatcgctag | 1320 |
| taatcgtaga | tcagaatgct | acggtgaata | cgttcccggg | ccttgtacac | accgcccgtc | 1380 |
| acaccatggg | agtgggttgc | aaaagaagta | ggtagcttaa | ccttcgggag | ggcgcttacc | 1440 |
| actttgtgat | tcatgactgg | gggggaagtc | gtaacaaggt | aacggtaggg | g | 1491 |

MICROBIAL METHOD FOR THE BIOTRANSFORMATION OF COLCHICINOID COMPOUNDS

FIELD OF INVENTION

The present invention relates to a gram negative bacteria having trans-glycosylation ability to convert colchicine derivatives to colchicocides and a process thereof. The present invention further relates to colchicine derivatives and a process for their production. It relates more particularly to the transformation of colchicinoid compounds using a selective strain of microorganism. The process of the present invention provides colchicinoid compounds glycosylated exclusively at C-3 of the aromatic ring A of colchicinoid compounds such as colchicine, thiocolchicine and its derivatives thereof, complete conversion, purity and with good productivity.

BACKGROUND OF THE INVENTION

It is a known fact that microorganisms are capable of modifying a chemical compound for its own use or for an unknown reason. Several chemical entities have been modified microbiologically to get more pharmacologically potent compounds. Microbiological transformation of colchicinoids are reported in literature (*Antimicrobial Agents and Chemotherapy* 1981 19(3): 465-469).

Thiocolchicoside is a potent competitive antagonist of GABA (A) R function [gamma-aminobutyricacid (GABA) type A receptors]. It is a muscle relaxant and displays anti-inflammatory and analgesic properties. It also shows strong epileptogenic and convulsant activity.

The biotransformation of thiocolchicine in to its monoglycosylated forms at C-2 and C-3 position by the culture *Centella asiatica*, reported by Solet et. al. (Phytochemistry 33, 4, 817-820, 1993) is not specific and hence the final yields are poor. Several investigators using different microbial strains also had the same problem of non-selective nature of the transformation. Hufford. C. D. et al (J. Pharm. Sci., 68, 10, 1239-1242, 1979), in his studies with *Streptomyces griseus* and *S. spectabilis* and Bellet P. et al (GB-923421, 1959) with different strains of bacteria, fungi and actinomycetes, tried to biotransform colchicinoid compounds in to its 3-demethylated derivatives. Their study resulted in non specific conversion and poor productivity.

Recently, Bombardelli & Ponzone in their patents have done transformation work using *Bacillus megaterium*. (U.S. Pat. No. 6,150,140 and U.S. Pat. No. 6,372,458). Their studies reported the conversion of colchicinoid compounds into its 3-glycosyl forms using *Bacillus megaterium* a gram positive bacteria.

Other than the above mentioned literature, information on the transformation of colchicinoid compounds is few and sketchy. Now, in our studies, we found an altogether new species which has not been reported earlier for its transformation potential. This particular species is found in the gut of nematode and no other apparent use or role is so far mentioned in the literature.

SUMMARY OF THE INVENTION

The main object of the present invention is to provide a new microbial transformation method for easy, specific and quantitative production of the 3-O-glucosylthiocolchicinoid compounds.

Another object of the invention is to identify a microbial species which is capable of transforming colchicinoid compounds in to 3-O-glycosyl derivatives with high productivity and purity.

In an embodiment, this invention discloses a transglycosylation function/biotransformation ability of species *Providencia vermicola*. The present inventors have found that the Thiocolchicine of formula (II)

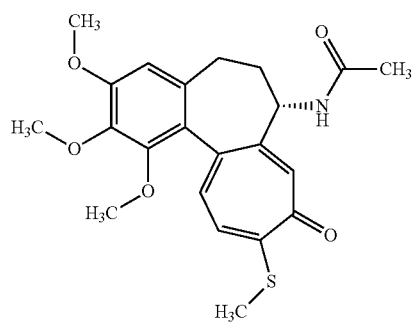 [SMILES: COc1cc2c(c(OC)c1OC)-c1ccc(SC)c(=O)cc1[C@@H](NC(C)=O)CC2]

Can be transformed into its corresponding demethylated form, Thiocolchicoside of formula (I)

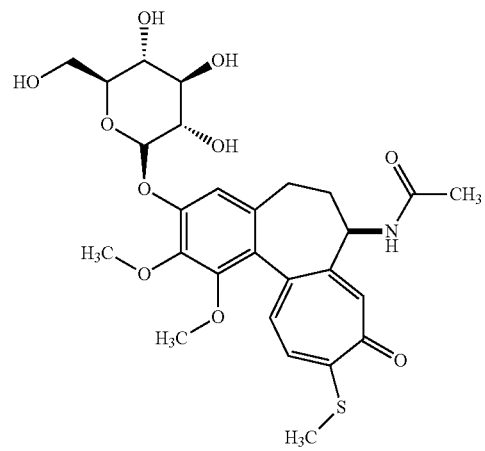

In another embodiment, the colchicinoid (colchicine or thiocolchicine) compound used in the aforementioned transformation is represented by a chemical formula (II)

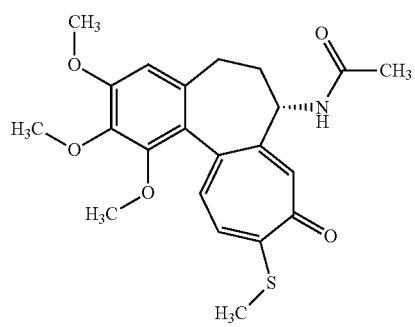 [SMILES: COc1cc2c(c(OC)c1OC)-c1ccc(SC)c(=O)cc1[C@@H](NC(C)=O)CC2]

In a further embodiment, the bacterial microorganism of the species *Providencia vermicola* STT-42-1 for the aforementioned transformation is a strain isolated from soil and deposited under strain number MTCC 5578 at The Microbial Type Culture Collection and Gene Bank (MTCC), Institute of Microbial Technology. Sector 39-A, Chandigarh-160036, India on Aug. 26, 2010. This biological deposit was made in accordance with the Budapest Treaty.

In further embodiment the strain designated as STT-42-1 (MTCC 5578) is newly identified and not described before in the literature for its biotransformation potential. This species was first isolated from the gut of a nematode as reported by Somvanshi et al 2006. The above mentioned strain belongs to the species *Providencia vermicola* based on microscopic and macroscopic appearance (colony morphological characters), based on chemotaxonomic classification (fatty acid profile) and based on 16S rRNA sequencing. Accordingly, the present invention also relates to the bacterial strain *Providencia vermicola* STT-42-1 as deposited under MTCC 5578 at the IMTECH (Institute of Microbial Technology—a Council of Scientific and Industrial Research organization), Chandigargh, India.

In further embodiment 16S rRNA gene sequence of the strain *Providencia vermicoloa* MTCC 5578 is:

mentioned above from the fermentation broth after transformation of the colchicinoid compounds as defined above with a member of the species *Providencia vermicola*. The extraction and isolation process from the fermentation medium comprises the steps of:

Obtaining the filtered/clarified broth from the fermentation medium free from bacterial cells, and other media components, bacterial associated debris and other insoluble substances.

Addition of an alcohol to recover the product in liquid fraction and precipitate other unwanted solids Concentration of the liquid portion either by microfiltration or by vacuum evaporation and repeated extraction with methylene chloride.

The solvent fraction is then adsorbed on a cation exchange resin and eluted with an alcohol to obtain the product The final step involves crystallization The present invention involves the screening of more than 200 microorganisms belonging to different classes of bacteria, fungi and actinomycetes. Among them one bacterial

```
TCAGATTGAACGCTGCGGCAGGCCTAACACATGCAAGTCGAGCGGTAACAGGGGAAGCTTGCTTCC

CGCTGACGAGCGGCGGACGGGTGAGTAATGTATGGGGATCTGCCCGATAGAGGGGGATAACTACG

GAAACGGTGGCTAATACCGCATAATCTCTTAGGAGCAAAGCAGGGGAACTTCGGTCCTTGCGCTATC

GGATGAACCCATATGGGATTAGCTAGTAGGTGGGGTAATGGCTCACCTAGGCGACGATCCCTAGCT

GGTCTGAGAGGATGATCAGCCACACTGGGACTGAGACACGGCCCAGACTCCTACGGGAGGCAGCAG

TGGGGAATATTGCACAATGGGCGCAAGCCTGATGCAGCCATGCCGCGTGTATGAAGAAGGCCCTAG

GGTTGTAAAGTACTTTCAGTCGGGAGGAAGGCGTTGATGCTAATATCATCAACGATTGACGTTACCGA

CAGAAGAAGCACCGGCTAACTCCGTGCCAGCAGCCGCGGTAATACGGAGGGTGCAAGCGTTAATC

GGAATTACTGGGCGTAAAGCGCACGCAGGCGGTTGATTAAGTTAGATGTGAAATCCCCGGGCTTAA

CCTGGGAATGGCATCTAAGACTGGTCAGCTAGAGTCTTGTAGAGGGGGGTAGAATTCCATGTGTAGC

GGTGAAATGCGTAGAGATGTGGAGGAATACCGGTGGCGAAGGCGGCCCCCTGGACAAAGACTGAC

GCTCAGGTGCGAAAGCGTGGGGAGCAAACAGGATTAGATACCCTGGTAGTCCACGCTGTAAACGAT

GTCGATTTGGAGGTTGTGCCCTTGAGGCGTGGCTTCCGGAGCTAACGCGTTAAATCGACCGCCTGGG

GAGTACGGCCGCAAGGTTAAAACTCAAATGAATTGACGGGGCCCGCACAAGCGGTGGAGCATGTG

GTTTAATTCGATGCAACGCGAAGAACCTTACCTACTCTTGACATCCAGAGAACTTAGCAGAGATGCT

TTGGTGCCTTCGGGAACTCTGAGACAGGTGCTGCATGGCTGTCGTCAGCTCGTGTTGTGAAATGTTG

GGTTAAGTCCCGCAACGAGCGCAACCCTTATCCTTTGTTGCCAGCGATTCGGTCGGGAACTCAAAGG

AGACTGCCGGTGATAAACCGGAGGAAGGTGGGGATGACGTCAAGTCATCATGGCCCTTACGAGTAG

GGCTACACACGTGCTACAATGGCGTATACAAAGAGAAGCGACCTCGCGAGAGCAAGCGGAACTCAT

AAAGTACGTCGTAGTCCGGATTGGAGTCTGCAACTCGACTCCATGAAGTCGGAATCGCTAGTAATCG

TAGATCAGAATGCTACGGTGAATACGTTCCCGGGCCTTGTACACACCGCCCGTCACACCATGGGAGT

GGGTTGCAAAAGAAGTAGGTAGCTTAACCTTCGGGAGGGCGCTTACCACTTTGTGATTCATGACTGG

GGGGGAAGTCGTAACAAGGTAACGGTAGGGG
```

In yet another embodiment, the present invention explains an efficient method of extracting and isolating the desired glycosylated compounds of formula (formula of thiocolchicoside and Colchicoside defined above from fermentation broth. Accordingly the present invention also relates to a process for the isolation of said 3-O-glycosyl derivatives strain belonging to *Providencia vermicola* has high capability and specificity to convert the colchicinoid compound to glycosylated at C-3 position of the aromatic ring. Further, the use of crude material having less purity getting converted to its glycosylated form is also having an advantage over use of pure substances.

DESCRIPTION OF DRAWINGS

FIG. 1: Sequence listing of gene sequence of the strain *Providencia vermicoloa* MTCC 5578.

DETAILED DESCRIPTION

Accordingly, the present invention relates to a biotransformation process, using selected microbial strain for the preparation of 3-O-glycosyl derivatives of colchicinoid compounds. The species *Providencia vermicola* is a gram negative rod. Its colonies are circular, entire, convex, with smooth surface forming creamy and pale yellow colored pigment. The isolated strain is capable of growing in high concentrations of Colchicine and Thiocolchicine.

The process of cultivating a microorganism is well known to the person skilled in the art. The microorganism is typically inoculated into a sterilized nutrient medium. The inoculum is typically obtained from frozen culture prepared earlier form a growth media or the inoculum is derived from a patch of slant. Optionally, a second stage culture is prepared by inoculating culture from the earlier stage. The second stage culture thus produced is then transferred to the conversion media, preferably after initial log phase of growth, the starting substance—a compound of Formula (II) or their derivatives—is then added to the conversion media. The concentration is affected by the organism after addition of compound of formula II mentioned below and then converted to Compound of formula I. After the reaction has been terminated, the transformed mixture of substance is purified by an established method or according to the present invention.

The described process is based on the discovery that the bacteria of the species *Providencia vermicola* is capable of glycosylating the colchicinoid compounds. This particular strain isolated from natural sources is capable of transforming the colchicinoid compounds or can tolerate these compounds in the presence of other carbon sources.

Accordingly, the present process for producing 3-O-glycosyl derivatives from colchicinoid compounds consists of fermenting a corresponding colchicinoid compound with the species *Providencia vermicola*. In one embodiment the strain *Providencia vermicola* STT-42-1 is as deposited under MTCC 5578 at the MTCC, Institute of Microbial Technology (IMTECH), Chandigarh, India.

Mutants derived from this strain by physical mutagens (e.g. like like UV, gamma irradiation) or chemical means (e.g like NTG, EMS) or molecular biological techniques can also be used in the process of invention. Alternatively, the enzyme or enzymes involved in this invention's biotransformation process can also be extracted from the bacterial biomass or from the fermented growth media and used in the biotrasformation by making the desired substrate come in contact with the enzyme system. Further, the bacterial system or the enzyme/s itself can be immobilized on suitable supporting matrix.

The process of this invention can be performed under the similar conditions as employed for the biotransformation of colchicinoid compounds with a bacterial species *Bacillus megaterium* as disclosed in the U.S. Pat. No. 6,150,140.

The strain MTCC5578 can be grown in typical microbiological substrates, containing organic nitrogen sources (such as peptones, soya peptones, yeast extracts, tryptone, meat extract, beef extract, etc), carbon sources (glucose, fructose, dextrin, glycerol, etc) at a pH of 4.0 to 9.0, preferably 6-7. The incubation temperature ranges from 15° C. to 45° C., preferably 25° C. to 35° C.

The carbon sources used can be in the range of 5 to 40% 10% to 80%, preferably from 10 to 40% and the nitrogen sources in the range of 2-10%, preferably in the range of 4-6%.

It is to be noted that the organism of the present invention is not reported in literature for its biotransformation potential however the organism was first isolated from a nematode as reported by somvanshi et al in *International Journal of systemic and evolutionary microbiology* (2006) 56, 629-633.

Accordingly, the present invention describes a process wherein the said process comprises invitro transformation of a colchicinoid compound into its glycosylated form comprising contacting a colchicinoid compound with a strain of *Providencia vermicola* at a temperature of between about 15° C. to about 45° C., at a pH level between 4 to 9 and for a sufficient time to produce the glycosylated form; and Isolating the glycosylated colchicinoid compound.

1. The strain of of *Providencia vermicola* is STT-42-1 as deposited under MTCC 5578 at the MTCC, Institute of Microbial Technology (IMTECH) Council of Scientific and Industrial Research Organization, Govt. of India, Chandigarh, India, having been designated as STT-42-1 (MTCC 5578) as stated earlier. The glycosylation to Thiocolchicine takes place at C-3 position of the aromatic ring producing Thiocolchicoside. The concentration of Thiocolchicine, a colchicinoid is above 0.1 g/L to 3.00 gm/L. The colchicinoid compound is selected from the group consisting of colchicines, thiocolchicine and the like. Thiocolchicine is converted to Thiocolchicoside using *Providencia vermicola* in the water based complex medium with peptone, yeast extract, bile salts, casein, hydrolyzed casein, whey proteins, gluten in combination with sugars viz. glucose, hydrolyzed starch, glycerol and other sugars. The conversion of Thiocolchicine to Thiocolchicoside is carried out using *Providencia vermicola* in the water based minimal medium with the salts of Ammonium Chloride, Ammonium Sulphate, di-ammonium phosphate, Phosphate salts of potassium, sodium, magnesium etc. along with sugars viz. glucose, hydrolyzed starch, soluble potato starch, glycerol, and other fermentable sugars etc. The water suspended solid Thiocolchicine to Thiocolchicoside is converted using *Providencia vermicola* enzymatic trans-glycosylation mechanism when added in the media in presence of Glucose or any other monosugars to get the respective product in 12 to 36 hrs. The enzymatic trans-glycosylation reaction using *Providencia vermicola* is carried out for converting Thiocolchicine to Thiocolchicoside by solubilizing Thiocolchicine in methanol, ethanol, and other alcohols or other suitable solvents and adding to the media in the presence of Glucose or any other monosugars to get the respective product in 12 to 36 hrs. The enzymatic trans-glycosylation process for conversion of Thiocolchicine to Thiocolchicoside is carried out either in solution with methanol, ethanol etc. or in suspended solid doses in water under sterile conditions along with Glucose during the fermentation process in 18 to 30 hrs.

EXAMPLE-1

Soil sample collected from different places in Karnataka state, India were used for the isolation of microorganisms. A known quantity of sample is suspended in sterile 0.05% tween 20 solution and dilutions prepared. The suspensions at different dilutions were plated on Nutrient agar and Potato Dextrose agar containing 1 g/l of Thiocolchcine or Colchicine. The plates were then incubated at 25° C. for PDA and 32° C. for NA in the dark for 24 to 120 hrs. The colonies growing in the plates were then transferred to another plate or slant and tested for bioconversion. The isolated pure cultures of bacteria were inoculated in a media containing per liter Glucose 10-20 g; Peptone 5-8 g; yeast Extract 4-8 g; colchicine or thiocolchicine 0.2 g and grown for 24-72 hrs and transferred to a fresh media containing glucose 30 g; Peptone 10 g; yeast extract 5 g; containing 0.5 g/L colchicine or thiocolchicine and grown for 72 to 120 at 29° C. in a rotary shaker at 150 RPM. The above procedure is followed to identify the possible isolates capable of converting colchicinoid compounds. Promising isolates capable of even slightest indication of conversion were identified and each one of the isolate was grown in a gradient plate for checking its tolerance and transferring those colonies having high tolerability to fresh liquid media containing 0.5 to 3.0 g/L colchicinoid compound. The fermentation cycle was monitored every 4 hrs till the conversion is observed and thereafter every two hrs for the progress as well as the carbon and nitrogen content of the fermentation broth. On successful completion of the above trial the isolates were further shortlisted and tested for confirmation. All the while, the promising isolates were grown continuously in conversion media containing increasing concentration of colchicinoid compound.

EXAMPLE-2

Production of Thiocolchicoside in Shake Flask

One WCB (Working Cell Bank) vial of 1 ml inoculum is aseptically transferred to a sterile 500 ml flask containing 100 ml of seed medium (TVM-1).

| Seed Medium TVM-1 | | |
|---|---|---|
| S. No | Ingredients | g/L |
| 1 | Glucose | 10 |
| 2 | Peptone | 5 |
| 3 | Yeast Extract | 2 |
|  | pH | 7.0 | pH not adjusted.

Medium was sterilized at 121° C. for 15 minutes. After inoculation, the flask was incubated at 29° C. and shaken at 200 RPM for 24 hrs. The OD reaching 10-15 indicates good growth. The seed on achieving the above parameters were transferred at 1-10% inoculum to conversion media (TCM). Conversion media was dispensed at 100 ml media in 500 ml conical flask.

| Conversion Medium TCM-1 | | |
|---|---|---|
| S. No | Ingredients | g/L |
| 1 | Glucose | 30 |
| 2 | Peptone | 10 |
| 3 | Yeast Extract | 5 |
|  | pH | 7.0 |

The conversion media was incubated at 29° C. at 200 rpm for 24 hrs. Every 4 hours samples were taken and tested by TLC for the conversion of Thiocolchicine. TLC was performed by spotting the samples on a Silica gel TLC $F_{254}$ and eluting with acetone:Ethyl acetate:water in the ratio of 5:4:1. For quantitative estimation, reverse phase HPLC analysis with isocratic elution with water:methanol 60:40 system was performed. For extraction, 1 ml sample is extracted with 4 ml of methanol and shaken vigorously. The sample is then centrifuged at 3000 rpm for 5 minutes and supernatant is used for HPLC and or TLC analysis.

EXAMPLE-3

One loopful of inoculum from a slant is transferred to seed medium TVM-2 and grown overnight for 18 hrs at 29° C. in a shaker at 150 RPM. On achieving good growth seed was transferred to conversion medium (TVM-2)

| Seed Medium-TVM-2 | | |
|---|---|---|
| S. No | Ingredients | g/L |
| 1 | Glucose | 10 |
| 2 | Tryptone | 5 |
| 3 | Yeast Extract | 2 |
|  | pH | 7.0 |

A conversion medium of TVM-2 of below mentioned concentration was prepared dispensed at 100 ml per 1 liter conical flask and sterilized for 15 minutes at 121° C. The seed medium, on maturation 5% of the seed medium transferred to conversion medium TVM-2. The flasks were incubated at 29° C. at 150 rpm for 72 hrs. Thiocolchicine was added 1 g/L at the time of inoculation. Conversion was checked from Log 24 hrs for every 4 hrs till complete conversion is achieved.

| Conversion medium TCM-2 | | |
|---|---|---|
| S. No | Ingredients | g/L |
| 1 | Glucose | 30 |
| 2 | Tryptone | 10 |
| 3 | Yeast Extract | 5 |
|  | pH | 7.0 |

On completion of conversion broth was centrifuged and the supernatant was stored at 4° C. for not more than 24 hrs and the product is extracted as explained in example-6.

EXAMPLE-4

Production of Thiocolchicoside in 10 L Fermentor

One WCB vial of 1 ml inoculum is aseptically transferred to a sterile 500 ml flask containing 100 ml of seed medium (TVM-1).

| Seed Medium TVM-1 | | |
|---|---|---|
| S. No | Ingredients | g/L |
| 1 | Glucose | 10 |
| 2 | Peptone | 5 |
| 3 | Yeast Extract | 2 |
|  | pH | 7.0 |

Medium was sterilized at 121° C. for 15 minutes. After inoculation, the flask was incubated at 29° C. and shaken at 200 RPM for 24 hrs. The OD reaching 10-15 indicates good growth. The seed on achieving the above parameters were transferred at 1-10% inoculum to conversion media (TCM).

| Conversion Medium TCM-1 | | |
|---|---|---|
| S. No | Ingredients | g/L |
| 1 | Glucose | 30 |
| 2 | Peptone | 10 |
| 3 | Yeast Extract | 5 |
|  | pH | 7.0 |

Conversion media was prepared in a 10 Liter fermentor with 7 liters of media. The fermentor was run at 30° C. for 24 to 30 hrs. RPM maintained in the range of 200 to 600, while the DO2% was maintained above 10% throught the cycle. Aeration was maintained between 0.5 vvm to maximum of 1 vvm. Backpressure was maintained between 0.5 bar to 1.0 bar. RPM, aeration and back pressure were increased gradually to maintain the dissolved oxygen levels in the fermenter.

Every 4 hours samples were taken and tested by TLC for the conversion of Thiocolchicine. TLC was performed by spotting the samples on a Silica gel TLC F254 and eluting with acetone:Ethyl acetate:water in the ratio of 5:4:1. For quantitative estimation, reverse phase HPLC analysis with isocratic elution with water:methanol 60:40 system was performed. For extraction, 1 ml sample is extracted with 4 ml of methanol and shaken vigorously. The sample is then centrifuged at 3000 rpm for 5 minutes to separate the solids and supernatant is used for HPLC or TLC analysis. The fermentor is harvested on completion of the conversion.

EXAMPLE-5

Production of Thiocolchicoside in 22 L Fermentor

One WCB vial of 1 ml inoculum is aseptically transferred to a sterile 500 ml flask containing 100 ml of seed medium (TVM-1).

| Seed Medium TVM-1 | | |
|---|---|---|
| S. No | Ingredients | g/L |
| 1 | Glucose | 10 |
| 2 | Peptone | 5 |
| 3 | Yeast Extract | 2 |
|  | pH | 7.0 |

Medium was sterilized at 121° C. for 15 minutes. After inoculation, the flask was incubated at 29° C. and shaken at 200 RPM for 24 hrs. The OD reaching 10-15 indicates good growth. The seed on achieving the above parameters were transferred at 1-10% inoculum to conversion media (TCM).

| Conversion Medium TCM-1 | | |
|---|---|---|
| S. No | Ingredients | g/L |
| 1 | Glucose | 30 |
| 2 | Peptone | 10 |
| 3 | Yeast Extract | 5 |
|  | pH | 7.0 |

Conversion media was prepared in a 22 Liter fermentor with 15 liters of media. The fermentor was run at 30° C. for 24 to 30 hrs. RPM maintained in the range of 200 to 600, while DO2% was maintained above 10% throughout the cycle. Aeration was maintained between 0.5 vvm to maximum of 1 vvm. Backpressure was maintained between 0.5 b to 1.0 b. RPM, aeration and back pressure were increased gradually to maintain the DO2%.

Every 4 hours samples were taken and tested by TLC for the conversion of Thiocolchicine. TLC was performed by spotting the samples on a Silica gel TLC F254 and eluting with acetone:Ethyl acetate:water in the ratio of 5:4:1. For quantitative estimation, reverse phase HPLC analysis with isocratic elution with water:methanol 60:40 system was performed. For extraction, 1 ml sample is extracted with 4 ml of methanol and shaken vigorously. The sample is then centrifuged at 3000 rpm for 5 minutes to separate the solids and supernatant is used for HPLC or TLC analysis. The fermentor is harvested on completion of the conversion.

EXAMPLE-6

Isolation of Thiocolchicoside

After reaching 30 hrs or when the conversion is complete (more than 95%), the biomass is separated by centrifuging at 3000 rpm for 10 minutes or the broth is micro filtered to get the clear supernatant. The supernatant was then concentrated by nano filtration or by vacuum evaporation to reduce the volume to minimum. To the reduce volume, at least 5 portions of methanol is added, stirred well and allowed to settle the solids or the solution was centrifuged to separate the precipitated solids. The clear supernatant is then concentrated to minimum and extracted repeatedly with methylene chloride. After clarification with silica gel, the suspension is concentrated under vacuum and left to crystallize.

$^1$H-NMR (DMSO-$d_6$) δ (ppm): 1.80 (3H-17, s); 2.38 (3H-18, m); 2.24 (H, m); 2.48 (4H-5a\5b, 6a\6b, m), 3.14-3.63 (sugar protons, 2'\3',4', 3H, m); 3.81 (3H, 13-OMe, s), 4.28 (H-7, m), 4.32 (2H, 6', m), 4.65 ( ), 4.91 (g-1'H, d, 6.2 Hz), 5.07 (5'H, dd, 3.2, 4.6 Hz), 5.36, (OH, d, 3.8 Hz) 6.83 (H-4, s), 6.99 (H-8, s), 7.12 (H-12, d, 10.1 Hz), 7.25 (H-8, d, 10.1 Hz), 8.60 (NH, d, 6.8 Hz).

$^{13}$C NMR (DMSO-$d_6$): 181.7, 169.2, 157.9, 151.6, 151.5, 150.8, 141.6, 137.9, 134.5, 134.6, 128.3, 127.1, 126.9, 111.5, 100.7, 77.7, 77.3, 73.9, 70.3, 61.5, 61.2, 56.5, 51.9, 36.0, 29.7, 22.9, 14.8.

(+)-ESI HRMS: m/z=564.2031 (M+H), 586.1724 [M+Na]$^+$, (Calcd 586.1723 for $C_{27}H_{33}NO_{10}S$)

All Chemical assignments are reported δ (ppm) downfield with respect to TMS.

SEQUENCE LISTING

<160> NUMBER OF SEQ ID NOS: 1

<210> SEQ ID NO 1
<211> LENGTH: 1491
<212> TYPE: DNA

-continued

```
<213> ORGANISM: Providencia vermicoloa

<400> SEQUENCE: 1
tcagattgaa cgctgcggca ggcctaacac atgcaagtcg agcggtaaca gggggaagctt      60 gcttcccgct gacgagcggc ggacgggtga gtaatgtatg gggatctgcc cgatagaggg     120
ggataactac ggaaacggtg gctaataccg cataatctct taggagcaaa gcaggggaac     180
ttcggtcctt gcgctatcgg atgaacccat atgggattag ctagtaggtg gggtaatggc     240
tcacctaggc gacgatccct agctggtctg agaggatgat cagccacact gggactgaga     300
cacggcccag actcctacgg gaggcagcag tggggaatat tgcacaatgg gcgcaagcct     360
gatgcagcca tgccgcgtgt atgaagaagg ccctagggtt gtaaagtact ttcagtcggg     420
aggaaggcgt tgatgctaat atcatcaacg attgacgtta ccgacagaag aagcaccggc     480
taactccgtg ccagcagccg cggtaatacg gagggtgcaa gcgttaatcg gaattactgg     540
gcgtaaagcg cacgcaggcg gttgattaag ttagatgtga atccccggg  cttaacctgg     600 gaatggcatc taagactggt cagctagagt cttgtagagg ggggtagaat tccatgtgta     660
gcggtgaaat gcgtagagat gtggaggaat accggtggcg aaggcggccc cctggacaaa     720
gactgacgct caggtgcgaa agcgtgggga gcaaacagga ttagataccc tggtagtcca     780
cgctgtaaac gatgtcgatt tggaggttgt gcccttgagg cgtggcttcc ggagctaacg     840
cgttaaatcg accgcctggg gagtacggcc gcaaggttaa aactcaaatg aattgacggg     900
ggcccgcaca gcggtggag  catgtggttt aattcgatgc aacgcgaaga accttaccta     960
ctcttgacat ccagagaact tagcagagat gctttggtgc cttcgggaac tctgagacag    1020
gtgctgcatg gctgtcgtca gctcgtgttg tgaaatgttg ggttaagtcc cgcaacgagc    1080
gcaaccctta tcctttgttg ccagcgattc ggtcgggaac tcaaaggaga ctgccggtga    1140
taaaccggag gaaggtgggg atgacgtcaa gtcatcatgg cccttacgag tagggctaca    1200
cacgtgctac aatggcgtat acaaagagaa gcgacctcgc gagagcaagc ggaactcata    1260
aagtacgtcg tagtccggat tggagtctgc aactcgactc catgaagtcg gaatcgctag    1320
taatcgtaga tcagaatgct acggtgaata cgttcccggg ccttgtacac accgcccgtc    1380
acaccatggg agtgggttgc aaaagaagta ggtagcttaa ccttcgggag ggcgcttacc    1440
actttgtgat tcatgactgg gggggaagtc gtaacaaggt aacggtaggg g             1491
```

We claim:

1. A process for in vitro transformation of a colchicinoid compound into a glycosylated colchicinoid compound, comprising:
   a. contacting said colchicinoid compound with a strain of *Providencia vermicola* at a temperature of between about 15° C. to about 45° C., at a pH of between 4 and 9 for a sufficient time to produce the glycosylated colchicinoid compound; and b. Isolating the glycosylated colchicinoid compound.

2. The process according to claim 1, wherein the strain of *Providencia vermicola* is STT-42-1 as deposited under MTCC 5578 at the MTCC, Institute of Microbial Technology (IMTECH) Council of Scientific and Industrial Research Organization, Govt. of India, Chandigarh, India, and designated as STT-42-1 (MTCC 5578).

3. A process for in vitro transformation of Thiocolchicine into a glycosylated colchicinoid compound, said glycosylated colchicinoid compound being Thiocolchicoside, comprising:

a. contacting said Thiocolchicine with a strain of *Providencia vermicola* at a temperature of between about 15° C. to about 45° C., at a pH of between 4 and 9 for a sufficient time to produce the Thiocolchicoside; and b. isolating the Thiocolchicoside.

4. The process according to claim 3, wherein the concentration of Thiocolchicine in said contacting step is between 0.1 gm/L and 3.00 gm/L.

5. The process according to claim 1, wherein the colchicinoid compound is selected from the group consisting of colchicines, thiocolchicine and mixtures thereof.

6. The process according to claim 3, wherein the conversion of Thiocolchicine to Thiocolchicoside using *Provicencia vermicola* is carried out in a water based complex medium comprising at least one substance selected from the group consisting of peptone, yeast extract, bile salts, casein, hydrolyzed casein, whey proteins, and gluten, said medium further comprising a sugar, hydrolyzed starch, or glycerol.

7. The process according to claim 3, wherein the conversion of Thiocolchicine to Thiocolchicoside using *Provicencia*

*vermicola* is carried out in a water based minimal medium comprising at least one salt selected from the group consisting of Ammonium Chloride, Ammonium Sulphate, di-ammonium phosphate, alkali metal phosphate salts, and alkaline earth metal phosphate salts, said medium further comprising a sugar, hydrolyzed starch, soluble potato starch, or glycerol.

8. The process according to claim 3, wherein the conversion of Thiocolchicine to Thiocolchicoside using *Provicencia vermicola* is carried out using water suspended solid Thiocolchicine by an enzymatic trans-glycosylation mechanism;

said conversion being carried out in the presence of Glucose to get Thiocolchicoside in 12 to 36 hrs.

9. The process according to claim 3, wherein an enzymatic trans-glycosylation reaction converting Thiocolchicine to Thiocolchicoside is carried out using *Providencia vermicola* by solubilizing the thiocolchicine in an alcohol;

said conversion being carried out in the presence of Glucose to get the Thiocolchicoside in 12 to 36 hrs.

10. The process according to claim 3, wherein an enzymatic trans-glycosylation process is carried out using *Providencia vermicola* for conversion of Thiocolchicine to Thiocolchicoside;

said process being carried out by dissolving the Thiocolchicine in an alcohol or suspending the Thiocolchicine in water under sterile conditions in the presence of Glucose and the *Providencia vermicola*; and allowing the enzymatic trans-glycosylation process to proceed for 18 to 30 hrs.

11. The process according to claim 3, wherein the glycosylation of Thiocolchicine takes place at the C-3 position of the aromatic ring and produces Thiocolchicoside.

12. The process according to claim 3, wherein the strain of *Providencia vermicola* is STT-42-1 as deposited under MTCC 5578 at the MTCC, Institute of Microbial Technology (IMTECH) Council of Scientific and Industrial Research Organization, Govt. of India, Chandigarh, India, and designated as STT-42-1 (MTCC 5578).

13. The process according to claim 1, wherein the conversion of the colchicinoid compound into the glycosylated colchicinoid compound using *Provicencia vermicola* is carried out in a water based complex medium comprising at least one substance selected from the group consisting of peptone, yeast extract, bile salts, casein, hydrolyzed casein, whey proteins, and gluten, said medium further comprising a sugar, hydrolyzed starch, or glycerol.

14. The process according to claim 1, wherein the conversion of the colchicinoid compound into the glycosylated colchicinoid compound using *Provicencia vermicola* is carried out in a water based minimal medium comprising at least one salt selected from the group consisting of Ammonium Chloride, Ammonium Sulphate, di-ammonium phosphate, alkali metal phosphate salts, and alkaline earth metal phosphate salts, said medium further comprising a sugar, hydrolyzed starch, soluble potato starch, or glycerol.

15. The process according to claim 1, wherein an enzymatic trans-glycosylation process is carried out using *Providencia vermicola* for conversion of the colchicinoid compound into the glycosylated colchicinoid compound;

said process being carried out by dissolving the colchicinoid compound in an alcohol or suspending the colchicinoid compound in water under sterile conditions in the presence of Glucose and *Providencia vermicola*; and allowing the enzymatic trans-glycosylation process to proceed for 18 to 30 hrs.

\* \* \* \* \*